US012076359B2

(12) United States Patent
Kim et al.

(10) Patent No.: US 12,076,359 B2
(45) Date of Patent: Sep. 3, 2024

(54) **PHARMACEUTICAL COMPOSITION COMPRISING A FRACTION OF *MELISSA OFFICINALIS* LEAF EXTRACT**

(71) Applicant: ANGIOLAB, INC., Daejeon (KR)

(72) Inventors: Min-Young Kim, Daejeon (KR); Byung Young Park, Daejeon (KR); Hee Suk Lee, Daejeon (KR); Hyung Soo Yuh, Sejong-Si (KR); Jeong Eun Kim, Daejeon (KR); Hyun Jeung Kim, Daejeon (KR)

(73) Assignee: ANGIOLAB, INC., Daejeon (KR)

( * ) Notice: Subject to any disclaimer, the term of this patent is extended or adjusted under 35 U.S.C. 154(b) by 0 days.

(21) Appl. No.: 18/381,023

(22) Filed: Oct. 17, 2023

(65) Prior Publication Data

US 2024/0041965 A1 Feb. 8, 2024

Related U.S. Application Data

(62) Division of application No. 17/427,168, filed as application No. PCT/KR2020/006669 on May 21, 2020, now abandoned.

(30) Foreign Application Priority Data

May 22, 2019 (KR) ........................ 10-2019-0060305

(51) Int. Cl.
*A61K 36/53* (2006.01)
*A61P 27/16* (2006.01)

(52) U.S. Cl.
CPC .............. *A61K 36/53* (2013.01); *A61P 27/16* (2018.01); *A61K 2236/333* (2013.01); *A61K 2236/39* (2013.01); *A61K 2236/51* (2013.01)

(58) Field of Classification Search
None
See application file for complete search history.

(56) References Cited

U.S. PATENT DOCUMENTS

| 10,894,071 | B2 | 1/2021 | Kim et al. |
| 11,224,629 | B2 | 1/2022 | Kim et al. |
| 2004/0009244 | A1 | 1/2004 | Kim et al. |
| 2010/0278914 | A1 | 11/2010 | Kim et al. |
| 2013/0243889 | A1 | 9/2013 | Morehouse |
| 2016/0199433 | A1 | 7/2016 | Pinkney et al. |

FOREIGN PATENT DOCUMENTS

| KR | 10-2009-0020285 A | 2/2009 |
| KR | 10-2014-0011209 A | 1/2014 |
| KR | 10-2015-0035245 A | 4/2015 |
| WO | WO-2004/052236 A2 | 6/2004 |

OTHER PUBLICATIONS

Office Action (Final) from corresponding U.S. Appl. No. 17/427,168, dated Dec. 5, 2023.
"Microcrystalline Cellulose" website (https://www.drugs.com/inactive/microcrystalline-cellulose-48.html#:':text=Microcrystalline%20cellulose%20is%20the%20same,suspending%20agent%20among%20other%20uses)—assessed Nov. 30, 2023.
International Search Report from corresponding PCT Application No. PCT/KR2020/006669, dated Sep. 9, 2020.
S De et al.; "Matrix metalloproteinases and their inhibitors in nonneoplastic otorhinolaryngological disease", The Journal of Laryngology & Otology, Jun. 2005, vol. 199, pp. 436-442.
Guginski, G., et al.; "Mechanisms involved in the antinociception caused by ethanolic extract obtained from the leaves of *Melissa officinalis* (lemon balm) in mice", Pharmacology, Biochemistry and Behavior, Apr. 7, 2009, vol. 93, pp. 10-16.
Wu, M-Y, et al.; "Nitric oxide syntheis is increased in the endometrial tissue of women with endometriosis", Human Reproduction, vol. 18, No. 12, pp. 2668-2671, 2003.
Extended European Search Report from corresponding European Patent Application No. 20810304.4, dated Apr. 14, 2023.
Office Action (Non-Final) from corresponding U.S. Appl. No. 17/427,168, dated Jul. 21, 2023.
Office Action from corresponding Japanese Patent Application No. 2021-551874, dated Mar. 19, 2024.
Jennings, C.R., et al.; "Matrix metalloproteinases 2 and 9 in otitis media with effusion", Clin. Otolaryngol. (May 18, 2001) vol. 26, issue 6, p. 491-494.
Jang, C.H., et al.; "Expression of matrix matalloproteinase-9 and -2 in pediatric chronic otitis media with effusion", Int. J. Pediatr. Otorhinolaryngol. (2006) vol. 70, issue 7, p. 1155-1158.

*Primary Examiner* — Susan Hoffman

(74) *Attorney, Agent, or Firm* — HARNESS, DICKEY & PIERCE, P.L.C.

(57) ABSTRACT

The present invention relates to a pharmaceutical composition for preventing or treating otitis media with effusion comprising a fraction of *Melissa officinalis* leaf extract as an effective ingredient.

3 Claims, 3 Drawing Sheets

[Fig. 1]
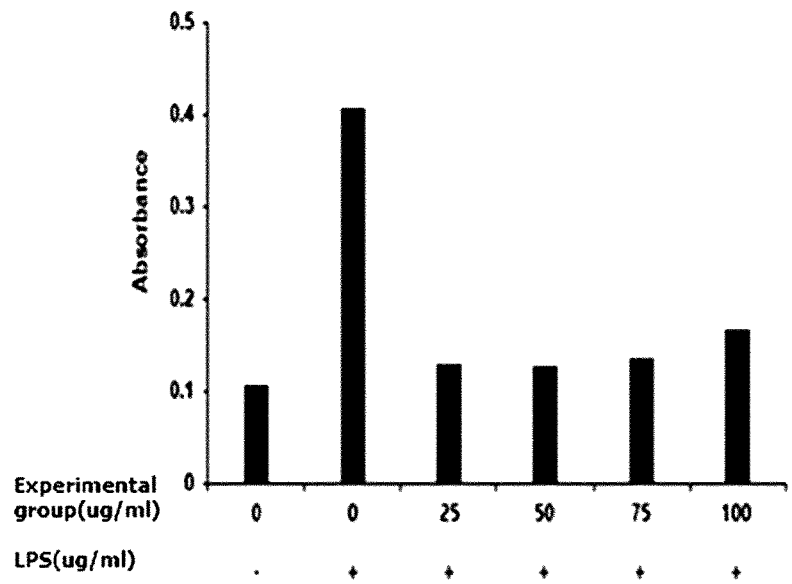
[Fig. 2]
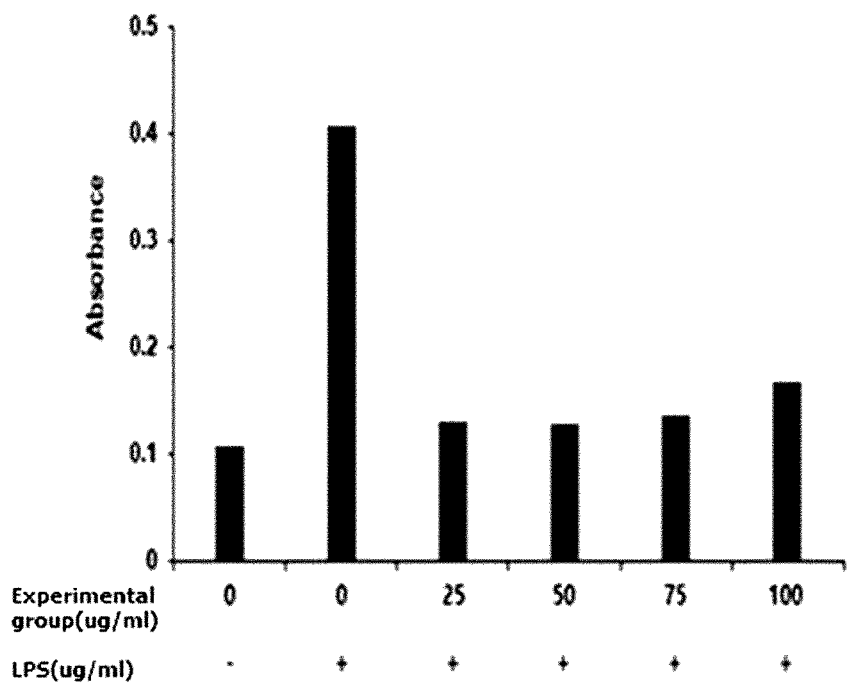
[Fig. 3]
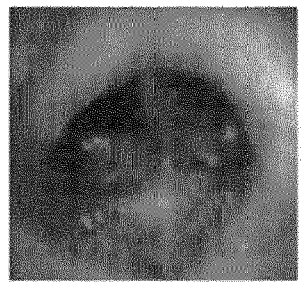
Typical OME (Grade II, ++)

[Fig. 4]
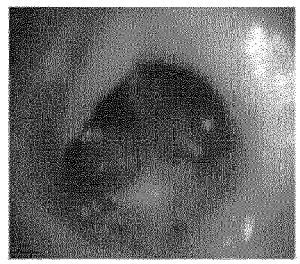
Dark blue OME (Grade I, +)
[Fig. 5]
Healed OME (Grade 0)
[Fig. 6]
Control group
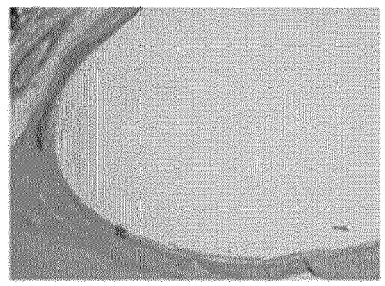
Experimantal group
[Fig. 7]
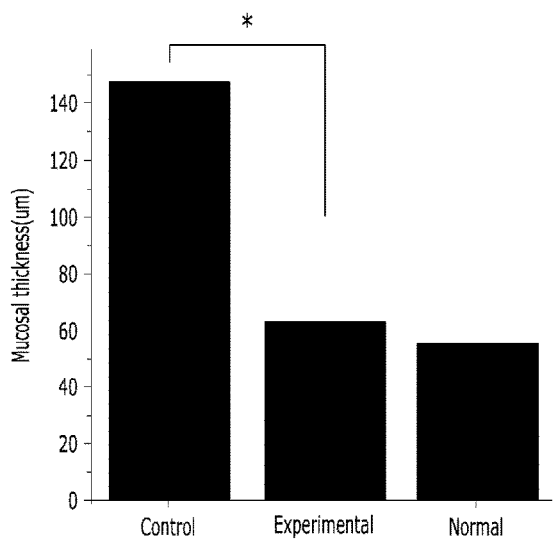
Asterisk p<0.05, t test

[Fig. 8]
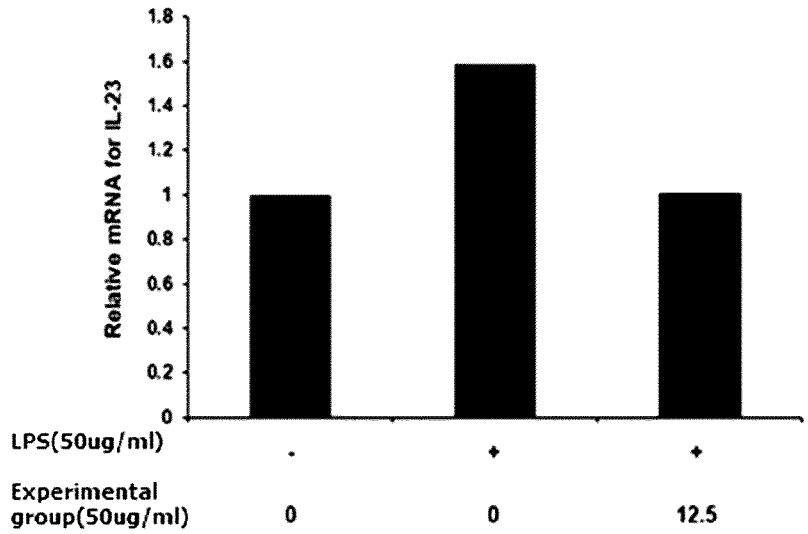
[Fig. 9]
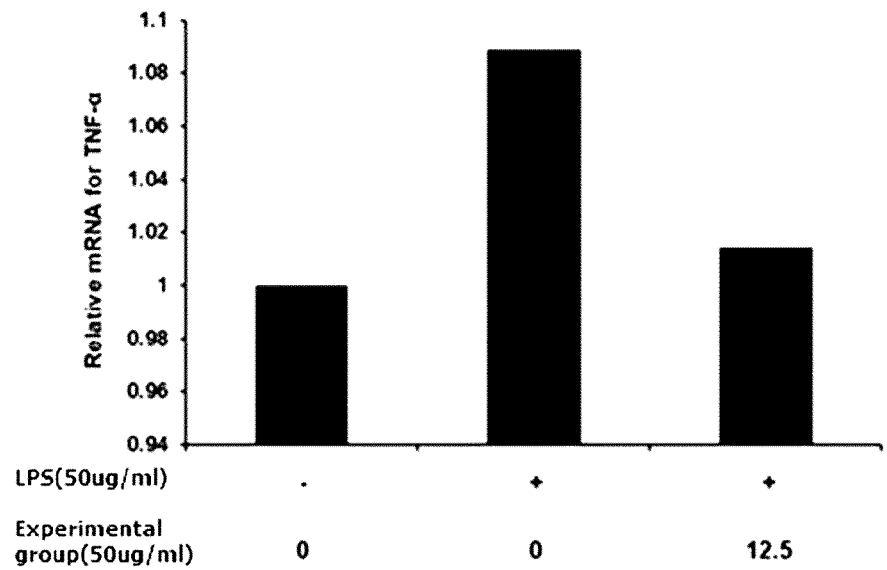

PHARMACEUTICAL COMPOSITION COMPRISING A FRACTION OF *MELISSA OFFICINALIS* LEAF EXTRACT

CROSS-REFERENCE TO RELATED APPLICATIONS

This application is a divisional of U.S. patent application Ser. No. 17/427,168, filed on 30 Jul. 2021, now abandoned, which is a national phase application of PCT Application No. PCT/KR2020/006669, filed on 21 May 2020, which claims the benefit and priority to Korean Patent Application No. 10-2019-0060305, filed on 22 May 2019. The entire disclosures of the applications identified in this paragraph are incorporated herein by references.

TECHNICAL FIELD

The present invention relates to a pharmaceutical composition comprising a fraction of *Melissa officinalis* leaf extract. More specifically, the present invention relates to a pharmaceutical composition for preventing or treating otitis media with effusion, comprising a fraction of *Melissa officinalis* leaf extract of the present invention as an effective ingredient.

BACKGROUND ART

*Melissa officinalis* is an herbaceous perennial plant, which belongs to the Labiatae family, and is also nicknamed Lemon Balm.

A *Melissa officinalis* leaf extract contains flavonoid, triterpene acids, volatile oils, glycosides of alcohol, phenol compounds and the like, as well as caffeic acid derivatives. In particular, the flavonoids contained in *Melissa officinalis* leaves are cynaroside, cosmosin, rhamnocitrin, isoquercitrin, etc., and ursolic acid as triterpene acid. The *Melissa officinalis* leaf extract contains hydroxycinnamic acid derivatives such as rosmarinic acid, which is one of non-volatile components drawing much attention these days, and also contains geraniol, neral, citronellal and eugenol as volatile oils.

An inflammation, which occurs in tympanic cavity, is called otitis media. Otitis media is roughly divided into acute otitis media and otitis media with effusion, of which about 40 to 50% is otitis media with effusion.

Otitis media with effusion frequently occurs to young children and old people. When eustachian tube function that connect the middle ear to the nasopharynx is deteriorated, a pressure control of inside and outside the eardrum becomes poor, and thus the middle ear comes to have a negative pressure, such that liquid is soaked out of a mucous membrane and stagnates. Thus, there occur symptoms such as difficulty in hearing, feeling of ear occlusion, etc. If acute upper respiratory inflammation, chronic sinusitis, allergic rhinitis, adenoidal hypertrophy and the like are present in a patient's background, an inflammation in a nose or a throat affects a middle ear through the eustachian tube all the time, and thus becomes chronic and prone to intractable. If otitis media with effusion becomes intractable, it may cause an after-effect such as difficulty in hearing, etc., thereby requiring a surgery. Thus, early treatment is considered important. In case of young children, it is difficult to frequently carry out a surgical procedure such as myringotomy, tympanostomy tube placement or the like. Thus, there is a need for a medicament to minimize a surgical procedure.

In general, the therapeutic agent used for otitis media with effusion mainly includes expectorants (for example, carbocysteine, etc.), macrolide antibiotics (for example, erythromycin ethylsuccinate, clarithromycin, etc.) or the like, but have failed to achieve a satisfactory effect. Thus, there is an urgent need for developing an oral agent with high efficacy.

PRIOR ART REFERENCES

Non-Patent Documents (Non-Patent Document 1) Human Reproduction Vol. 18, No. 12 pp. 2668-2671, 2003

DISCLOSURE OF INVENTION

Technical Problem

An objective of the present invention is to provide a pharmaceutical composition for preventing or treating otitis media with effusion, comprising a fraction of *Melissa officinalis* leaf extract.

Another objective of the present invention is to provide a method for preventing or treating otitis media with effusion by administering a therapeutically effective amount of a fraction of *Melissa officinalis* leaf extract to the subject in need thereof.

Still another objective of the present invention is to provide a use of a pharmaceutical composition comprising a fraction of *Melissa officinalis* leaf extract, in the manufacture of a medicament for preventing or treating otitis media with effusion.

Solution to Problem

The present inventors have recognized a need for study on prevention or treatment of otitis media with effusion and have achieved the objectives of the study on natural substances capable of preventing or treating this disease.

Specifically, the present inventors have found that the case of containing a fraction of *Melissa officinalis* leaf extract as an effective ingredient has an effect on prevention and treatment of otitis media with effusion, thereby completing the present invention.

The present invention provides a pharmaceutical composition for preventing or treating otitis media with effusion comprising a fraction of *Melissa officinalis* leaf extract.

It has been identified that the pharmaceutical composition comprising a fraction of *Melissa officinalis* leaf extract according to the present invention as an effective ingredient may prevent or treat otitis media with effusion in such a way that a middle ear effusion (MEE) is ameliorated, the MEE is reabsorbed and thus not observed, a thickness of middle ear mucosa is remarkably decreased, and IL-23 and TNF-α genes are significantly decreased when examining the expression of IL-23 and TNF-α genes.

Hereinafter, the present invention will be described in more detail.

The pharmaceutical composition for preventing or treating otitis media with effusion according to the present invention contains a fraction of *Melissa officinalis* leaf extract as an effective ingredient, which is obtained in such a way that *Melissa officinalis* leaves is extracted with 50 to 100% alcohol (v/v), concentrated, fractionated with ethyl acetate, and then dried to give a fraction of *Melissa officinalis* leaf extract.

Specifically, the fraction of *Melissa officinalis* leaf extract is obtained in such a way that *Melissa officinalis* leaves is extracted with 50 to 100% alcohol (v/v) and dried, and the alcohol extract is suspended with water, fractionated with ethyl acetate, and then dried, and the ethyl acetate fraction is resuspended with water and dried.

In the present specification, the term "pharmaceutical composition" is defined as a chemical or biological compound or substances, or a mixture or combination of at least two compounds or substances, which are intended to be used for medically diagnosing, dealing with, treating or preventing diseases or pathologies.

When preparing the fraction of *Melissa officinalis* leaf extract of the present invention, dried *Melissa officinalis* leaves, non-dried *Melissa officinalis* leaves or a mixture thereof may be used. For an effective extraction, the *Melissa officinalis* leaves may be used after being cut into small pieces.

In the present specification, the term "alcohol" means a compound in which a hydroxyl group is bound to a carbon atom of an alkyl or substituted alkyl group, the term "alkyl" means a linear saturated hydrocarbon group or a branched saturated hydrocarbon group, and the term "substituted alkyl group" means the one in which a substituent bonded to the carbon of an alkyl group is substituted with hydroxy, cyano, halo, etc.

In the present specification, the term "extract" includes an extract liquid itself and all dosage forms of extract which may be formed by using the extract liquid, such as the extract liquid obtained by carrying out an extraction on the *Melissa officinalis* leaves, a diluent or concentrate of the extract liquid, a dried matter obtained by drying the extract liquid, a crude purified product or a purified product of the extract liquid, a mixture thereof, or the like.

In the present specification, the term "fraction" means a product obtained by performing a fractionation to separate a specific component or a specific component group from a mixture comprising many different components.

In the present invention, a fractionation method of obtaining the fraction of extract is not specifically limited, and may be performed according to a method conventionally used in the art. Specifically, there are a solvent fractionation method performed by treating various solvents, a fractionation method using ultrafiltration performed by passing through an ultrafiltration membrane having a certain molecular weight cut-off value, a chromatography fractionation method performed with various chromatography types (manufactured for separation according to sizes, electric charges, hydrophobicity or affinity), a combination thereof, and the like. Specifically, there may be a method in which an extraction is performed on the *Melissa officinalis* leaves of the present invention, after which an obtained extract is treated with a pre-determined solvent so as to obtain a fraction from the extract.

In the present invention, the type of fractionation solvent used for obtaining the fraction are not specifically limited, and any solvents generally known in the art may be used. Specifically, it may be ethyl acetate, which is a non-polar solvent.

In the present specification, the term "effective ingredient" means including a main component as a substances or a substance group (including herb medicine, etc., of which a pharmacologically active component, etc., has not been identified yet) expected to directly or indirectly exhibit the efficacy and effect of a composition thereof by an intrinsic pharmacological action.

To prepare an alcohol extract of *Melissa officinalis* leaves, an extraction may be performed according to a conventional extraction method by using 50 to 100% alcohol (v/v), preferably 70 to 80% alcohol (v/v) in an amount of 5 to 15 times (v/w) of the *Melissa officinalis* leaves.

The alcohol refers to C1-C6 alcohol including ethanol, methanol, etc., preferably may be ethanol or methanol.

In the present specification, the term "C1-C6" means a functional group or a main chain having one or more and six or less carbon atoms.

In one embodiment of the present invention, a fraction of *Melissa officinalis* leaf extract was prepared by suspending 75% ethanol extract of the *Melissa officinalis* leaves in water, then fractionating with ethyl acetate and drying.

The fraction of *Melissa officinalis* leaf extract may be an ethyl acetate fraction of ethanol extract of *Melissa officinalis* leaves.

The method has an effect of effectively extracting a water-soluble material and a water-insoluble material and extracting the water-insoluble material having a low solubility to water, but having a high solubility to ethyl acetate, by using 50 to 100% alcohol (v/v).

Ethyl acetate is selected as a secondary extraction solvent of *Melissa officinalis* leaves by considering a yield, toxicity of a residual solvent, a relative content of a marker compound, etc.

For mass production of the fraction of *Melissa officinalis* leaf extract, the fraction of *Melissa officinalis* leaf extract may be prepared in large quantities according to a method of suspending 50 to 100% alcohol extract of *Melissa officinalis* leaves in water, then fractionating with ethyl acetate, and then freeze-drying or hot-air drying.

The fraction of *Melissa officinalis* leaf extract has a content of 20% to 80% by weight with regard to the total weight of the composition comprising the fraction of *Melissa officinalis* leaf extract.

The pharmaceutical composition of the present invention may contain the fraction of *Melissa officinalis* leaf extract as an effective ingredient and further comprises pharmaceutically acceptable carriers, and may be formulated to an oral dosage form such as powder, granule, tablet, capsule, suspension, emulsion, syrup, aerosol, etc., as well as a form of an external preparation and a sterile solution for injection according to a conventional method.

In the present specification, the term "pharmaceutically acceptable" refers to a composition which is physiologically acceptable and does not conventionally cause an allergic response such as gastrointestinal disturbance, dizziness, etc., or other responses similar thereto, when administered to humans.

In the present specification, the term "pharmaceutically acceptable carrier" typically includes the liquid or non-liquid basis of a pharmaceutical composition. If the pharmaceutical composition is provided in liquid form, the carrier will typically be pyrogen-free water, isotonic saline or buffer (aqueous) solutions, for example, phosphate, citrate, etc. The injection buffer may be hypertonic, isotonic or hypotonic with reference to the specific reference media. In other words, the buffer may have a higher, identical or lower salt content with reference to the specific reference media. Preferably, it is possible to use the concentration of the salt mentioned above, which do not lead to damage of cells due to osmosis or other concentration effects. The reference media are for example, liquid occurring in "in vivo" methods, such as blood, lymph, cytosolic liquid or other body liquids, or for example, liquids, which may be used as reference media in "in vitro" methods, such as common buffers or liquids. Such common buffers or liquids are known to a skilled person.

The pharmaceutically acceptable carriers may include the carriers conventionally used in the art, for example, lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil and the like, but are not limited thereto.

Also, the pharmaceutical composition of the present invention may contain a diluent or an excipient such as filler, extender, binder, humectant, disintegrant, surfactant, etc., or other pharmaceutically acceptable additives.

The pharmaceutical composition of the present invention may be prepared into forms of liquid, suspension, powder, granule, tablet, capsule, pill or extract.

The composition of the present invention may be administered orally or parenterally (for example, applied or injected intravenously, subcutaneously or intraperitoneally).

In the present specification, the term "oral administration" is a route of administration where the substance for ameliorating a pathological symptom is taken through the mouth. In the present specification, the term "parenteral administration" means a route of administration where the substance is administered subcutaneously, intramuscularly, intravenously and intraperitoneally through a tube, excluding administration through the mouth.

A solid preparation for oral administration may include powder, granule, tablet, capsule, soft capsule, pill, etc. A liquid preparation for oral administration may include a suspension, liquid for internal use, emulsion, syrup, aerosol, etc., but may also include various excipients, for example, humectant, sweetening agent, flavoring agent, preservative, etc. in addition to water and liquid paraffin, which are commonly used simple diluents.

A preparation for parenteral administration may be used by being formulated into a form of external preparation and sterilized injectable preparation such as sterilized aqueous solution, liquid, non-aqueous solvent, suspension, emulsion, eye drop, eye ointment, syrup, suppository, aerosol, etc., according to respective conventional methods, and may be preferably used by preparing a pharmaceutical composition of cream, gel, patch, spray, ointment, plaster, lotion, liniment, eye ointment, eye drop, paste or cataplasma, but is not limited thereto. A composition for local administration may be an anhydrous or aqueous form depending on a clinical prescription. As the non-aqueous solvent and the suspension, propylene glycol, polyethylene glycol, vegetable oil such as olive oil, injectable ester such as ethyl oleate, etc., may be used. As a base of the suppository, witepsol, macrogol, tween 61, cacao butter, laurinum, glycerogelatin, etc., may be used.

The pharmaceutically acceptable additive according to the present invention may be contained in an amount of 0.1 to 99.9 parts by weight, specifically in an amount of 0.1 to 50 parts by weight with regard to the composition, but is not limited thereto.

A preferred dosage of the composition of the present invention may vary depending on in vivo absorption degree of an active ingredient, a patient's age, sex and degree of obesity, but may be appropriately selected by a skilled person in the art. However, in case of oral administration for a preferable effect, the composition of the present invention may be generally administered to an adult at a dose of 0.0001 to 40 mg/kg a day, preferably 0.001 to 30 mg/kg a day.

The administration may be performed once a day or several times a day by dividing the preparation. The dosage above does not limit the scope of the present invention in any aspect.

Pharmaceutical Composition for Preventing or Treating Otitis Media with Effusion Comprising a Fraction of *Melissa officinalis* Leaf Extract The present invention provides a pharmaceutical composition for preventing or treating otitis media with effusion comprising a fraction of *Melissa officinalis* leaf extract.

In the present invention, the term "otitis media with effusion (OME)" means a disease in which a middle ear, a space inside an eardrum of an ear, is filled with liquid called effusion without any symptoms of earache, fever or the like.

The pharmaceutical composition for preventing or treating otitis media with effusion comprising a fraction of *Melissa officinalis* leaf extract according to the present invention as an effective ingredient has an effect of preventing or treating otitis media with effusion in such a way that middle ear effusion (MEE) is ameliorated, the effusion is reabsorbed and thus not observed, a thickness of a middle ear mucosa is remarkably decreased, and IL-23 and TNF-α genes are significantly decreased when examining the expression of IL-23 and TNF-α genes.

The pharmaceutical composition for preventing or treating otitis media with effusion comprising a fraction of *Melissa officinalis* leaf extract of the present invention as an effective ingredient may be administered in a conventional manner orally, rectally, intravenously, intra-arterially, intraperitoneally, intramuscularly, intrasternally, percutaneously, locally, intraocularly or through an intradermal route, and specifically may be orally administered.

It is preferable that the pharmaceutical composition for preventing or treating otitis media with effusion comprising a fraction of *Melissa officinalis* leaf extract of the present invention as an effective ingredient may be administered at a dose of 0.001 to 40 mg/kg when administered once to several times a day.

The fraction of *Melissa officinalis* leaf extract is the same as described above.

Prevention and Treatment Method

Another objective of the present invention is to provide a method for preventing or treating otitis media with effusion by administering a therapeutically effective amount of a fraction of *Melissa officinalis* leaf extract to the subject in need thereof.

In the present specification, the term "subject in need for treatment" means mammals such as monkey, cow, horse, dog, cat, rabbit, rat, mouse, etc., and in particular includes humans. The term "administration" means providing a desired substance to a patient through any appropriate method.

In the treatment method of the present invention, the pharmaceutical composition for preventing or treating otitis media with effusion comprising a fraction of *Melissa officinalis* leaf extract of the present invention as an effective ingredient may be administered in a common manner through orally, rectally, intravenously, intra-arterially, intraperitoneally, intramuscularly, intrasternally, percutaneously, locally, intraocularly or intradermal route, and specifically may be orally administered.

In the present specification, the term "therapeutically effective amount" means an amount of an effective ingredient or a pharmaceutical composition which induces a biological or medical response in a tissue system, animal or human being considered by a researcher, veterinarian, physician or other clinician, and which includes an amount that induces a relief of the symptoms of disease or disorder to be treated. It is apparent to those skilled in the art that the therapeutically effective dosage and the number of administration for effective ingredient of the present invention may vary depending on a desired effect. Thus, an optimal dosage to be administered may be easily determined by those skilled in the art, and may be adjusted depending on various factors including a type of disease, severity of disease, contents of effective ingredient and other component contained in a composition, a type of dosage form, a patient's age, body weight, general health condition, sex and diet, an administration time, an administration route, a secretion rate of the composition, a treatment period and concomitant drugs therewith. In the treatment method of the present invention, it is preferable for adults that the pharmaceutical composition for preventing or treating otitis media with effusion comprising a fraction of *Melissa officinalis* leaf extract of the present invention as an effective ingredient may be administered at a dose of 0.001 to 40 mg/kg when administered once to several times a day.

In the present specification, the term "prevention" refers to any act of inhibiting or delaying otitis media with effusion by administering the pharmaceutical composition according to the present invention.

In the present specification, the term "treatment" refers to any act of improving or beneficially altering otitis media with effusion by administering the pharmaceutical composition according to the present invention.

Use of Pharmaceutical Composition

An objective of the present invention is to provide a use of a pharmaceutical composition comprising a fraction of *Melissa officinalis* leaf extract, in the manufacture of a medicament for preventing or treating otitis media with effusion.

In one embodiment of the present invention, the pharmaceutical composition comprising a fraction of *Melissa officinalis* leaf extract in the manufacture of a medicament may be mixed with an acceptable carrier, etc. and further contain other agents.

The matters mentioned in the pharmaceutical composition, treatment method and use of the present invention are applied equally unless contradictory to each other.

Advantageous Effects of Invention

The pharmaceutical composition comprising a fraction of *Melissa officinalis* leaf extract according to the present invention as an effective ingredient may prevent or treat otitis media with effusion in such a way that a middle ear effusion (MEE) is ameliorated, the MEE is reabsorbed and thus not observed, a thickness of middle ear mucosa is remarkably decreased, and IL-23 and TNF-α genes are significantly decreased when examining the expression of IL-23 and TNF-α genes.

BRIEF DESCRIPTION OF DRAWINGS

FIG. 1 is a graph showing the results of an experiment on the inhibitory effects on NO production in LPS-induced inflammation in RAW 264.7 cells when treated with an experimental group (fraction of *Melissa officinalis* leaf extract according to Example 1) and a control group.

FIG. 2 is a graph showing the experiment results of inhibitory effects on IL-6 protein expression level in LPS-induced inflammation in RAW 264.7 cells when treated with an experimental group (fraction of *Melissa officinalis* leaf extract according to Example 1) and a control group.

FIG. 3 is a picture showing otitis media with effusion in an experimental model of SD white rat, which was induced by blocking a eustachian tube, according to one embodiment of the present invention.

FIG. 4 is a picture showing a therapeutic effect (Grade I) on otitis media with effusion in an experimental model of SD white rat, which was induced by blocking a eustachian tube, when administered with an experimental group (fraction of *Melissa officinalis* leaf extract according to Example 1), according to one embodiment of the present invention.

FIG. 5 is a picture showing a therapeutic effect (Grade 0) on otitis media with effusion in an experimental model of SD white rat, which was induced by blocking a eustachian tube, when administered with an experimental group (fraction of *Melissa officinalis* leaf extract according to Example 1), according to one embodiment of the present invention.

FIG. 6 is a picture showing results of histopathological findings on a middle ear cavity removed on a seventh day after blocking a eustachian tube after treated with an experimental group (fraction of *Melissa officinalis* leaf extract according to Example 1) and a control group (0.5% CMC).

FIG. 7 is a graph showing results of evaluating a thickness of middle ear mucosa after treated with an experimental group (fraction of *Melissa officinalis* leaf extract according to Example 1) and a control group (0.5% CMC).

FIG. 8 is a graph showing a decrease in IL-23 expression level when IL-23 genes up-regulated by LPS were treated with an experimental group (fraction of *Melissa officinalis* leaf extract according to Example 1).

FIG. 9 is a graph showing a decrease in TNF-α gene expression level when TNF-α genes up-regulated by LPS were treated with an experimental group (fraction of *Melissa officinalis* leaf extract according to Example 1).

MODE FOR THE INVENTION

The terms used herein have been selected from the general terms that are currently used as widely as possible while considering functions in the present invention, but this may be subject to change depending on the intention of those skilled in the art, precedents, the advent of new technologies, or the like. In addition, in certain cases, some terms are arbitrarily selected by the applicant. In this case, their meanings will be described in detail in the description of the corresponding invention. Thus, the terms used in the present invention should not be defined simply by the names of the terms, but should be defined based on the meanings of the terms and the contents provided throughout the present invention.

All the terms used herein including technical or scientific terms have the same meaning as commonly understood by those ordinary skilled in the art, to which the present invention pertains, unless defined otherwise. Such terms as those defined in a generally used dictionary are to be interpreted to have the meanings equal to the contextual meanings in the relevant art, and are not to be interpreted to have ideal or excessively formal meanings, unless clearly defined in the present application.

A numerical range includes the numerical value defined in the above range. All the maximum numerical limits given throughout the present specification include all the lower numerical limits thereof as if the lower numerical limits are clearly written. All the minimum numerical limits given throughout the present specification include all the higher numerical limits thereof as if the higher numerical limits are clearly written. All the numerical limits given throughout the present specification will include all the narrower numerical ranges thereof within a broader numerical range, as if the narrower numerical limits are clearly written.

The examples and the preparation examples are provided for better understanding of the present invention. The following examples and preparation examples are provided only for the purpose of illustrating the present invention, and thus the present invention is not limited thereto.

EXAMPLE

Example 1. Preparation of a Fraction of *Melissa officinalis* Leaf Extract 200 kg of dried *Melissa officinalis* leaves were extracted with reflux using 75% ethanol (v/v) in an amount of ten times by weight for 4 hours, then filtered through a cartridge filter, and then primarily concentrated under reduced pressure. An equal amount of ethyl acetate was added to the obtained concentrate and the process of fractionation was repeated twice. Then, an ethyl acetate layer was collected, and secondarily concentrated under reduced pressure, and dried, and then pulverized to obtain an ethyl acetate fraction of ethanol extract of *Melissa officinalis* leaves (yield: 8.2 kg).

Experimental Example 1. Inhibition of NO Production and Protein Expression Level (1) Experimental Method The fraction of *Melissa officinalis* leaf extract according to Example 1 was evaluated on the inhibition of NO production and the protein expression level of interleukin-6 (IL-6) in RAW 264.7 cells, which are murine macrophage cell lines stimulated by LPS.

With regard to evaluating the effect of the fraction of *Melissa officinalis* leaf extract according to Example 1 on the inhibition of NO production in RAW 264.7 cells stimulated by LPS, the RAW 264.7 cells were adjusted to 1×10$^6$ cells/mL, inoculated into a 24 well plate, and cultured at 37° C. 5% $CO_2$ incubator for 2 hours. After that, the cells were treated with the fraction of *Melissa officinalis* leaf extract according to Example 1 at 0, 25, 50, 75 and 100 ug/mL, then stimulated by LPS at 1 ug/mL in one hour later, and then main cultured for 24 hours. The obtained supernatant and Griess reagent (1% sulfanilamide+0.1% naphthylendiamine dihydrochloride, 1:1) were subjected to a reaction at 1:1 at room temperature for 10 minutes, and the absorbance was measured at 540 nm by using a microplate reader.

With regard to evaluating the effect of the fraction of *Melissa officinalis* leaf extract according to Example 1 on the protein expression level of interleukin-6 (IL-6) in RAW 264.7 cells stimulated by LPS, an amount of interleukin-6 (IL-6) secreted into the cell culture medium of RAW 264.7 cells was measured by using an ELISA kit (Mouse ELISA set, R&D Systems Inc.). To obtain the cell culture medium, the RAW 264.7 cells were adjusted to 5×10$^6$ cells/mL, and inoculated into a 24-well plate, and cultured for 2 hours, and then treated with the fraction of *Melissa officinalis* leaf extract according to Example 1 at each concentration of 0, 25, 50, 75 and 100 ug/mL as well as LPS at 1 ug/mL. After that, a main culture was performed for 24 hours, and then supernatant was obtained through centrifugation. For the enzyme-linked immunosorbent assay (ELISA), an anti-mouse IL-6 was seeded in a microplate as a capture antibody, and subjected to coating overnight at room temperature, and washed with wash buffer (#WA126, R&D Systems Inc.), and subjected to blocking with reagent diluent (#DY995, R&D Systems Inc.), and then washed with wash buffer. Then, the cell culture supernatant was seeded in each microplate well and subjected to a reaction at room temperature for 2 hours. After the reaction, washing was performed with wash buffer, after which a diluted biotinylated anti-mouse IL-6 detection antibody and streptavidin-horseradish peroxidase conjugate were added therein and subjected to a reaction at room temperature for 20 minutes. After that, washing was performed again with wash buffer, after which a substrate solution (#DY999, R&D Systems Inc.) was added and subjected to a dark reaction at room temperature for 20 minutes. Finally, the reaction was ended with a stop solution (#DY994, R&D Systems Inc.), after which the absorbance was measured at 450 nm by using a microplate reader.

(2) Effect on Inhibition of NO Production

The effect of the fraction of *Melissa officinalis* leaf extract according to Example 1 on the inhibition of NO production was examined through using LPS-induced inflammation model in RAW 264.7 cells.

TABLE 1

| | Absorbance (%) |
|---|---|
| Control | 26 |
| LPS 1 ug/mL | 100 |
| LPS 1 ug/mL + Experimental group 25 ug/mL | 32 |
| LPS 1 ug/mL + Experimental group 50 ug/mL | 31 |
| LPS 1 ug/mL + Experimental group 75 ug/mL | 34 |
| LPS 1 ug/mL + Experimental group 100 ug/mL | 41 |

Referring to FIG. 1, it was identified that an amount of nitric oxide (NO) was increased in the RAW 264.7 cells induced by LPS, and the NO production was inhibited in a concentration-dependent manner when those cells were treated with the fraction of *Melissa officinalis* leaf extract according to Example 1. The fraction of *Melissa officinalis* leaf extract according to Example 1 effectively inhibited NO production which was increased in the RAW 264.7 cells by LPS-induced inflammation model.

(3) Effect on IL-6 Protein Expression Level

The effect of the fraction of *Melissa officinalis* leaf extract according to Example 1 on the IL-6 protein expression level was examined through an experiment on the inhibition of IL-6 protein expression level in RAW 264.7 cells by LPS-induced inflammation model.

TABLE 2

| | IL-6 (%) |
|---|---|
| Control | 0.00 |
| LPS 1 ug/mL | 100.00 |
| LPS 1 ug/mL + Experimental group 25 ug/mL | 58.70 |
| LPS 1 ug/mL + Experimental group 50 ug/mL | 19.12 |
| LPS 1 ug/mL + Experimental group 75 ug/mL | 14.85 |
| LPS 1 ug/mL + Experimental group 100 ug/mL | 15.61 |

Referring to FIG. 2, it was identified that IL-6 protein expression level which was increased by LPS in RAW 264.7 cells was is decreased in a concentration-dependent manner when treated with the fraction of *Melissa officinalis* leaf extract according to Example 1. The fraction of *Melissa officinalis* leaf extract according to Example 1 effectively decreased the IL-6 protein expression level increased by LPS-induced inflammation in RAW 264.7 cells.

Experimental Example 2. Identification of Therapeutic Effect on Otitis Media with Effusion (1) Experimental Method
Experiment 1
In in vitro test, the effect of the fraction of *Melissa officinalis* leaf extract according to Example 1 on the expression of genes encoding inflammatory cytokines, interleukin (IL)-23 and tumor necrosis factor alpha (TNF-α) was examined after an inflammation was induced in human middle ear epithelial cells (HMEEC) by lipopolysaccharide (LPS).
Experiment 2
After incising a skin of male sprague-dawley (SD) white rat, a hole was made on a bony part of a eustachian tube (ET) to make a small pore therein, after which dental cement was injected into the small pore by using a disposable 1 mL syringe.

An observation was made on all the SD white rates by using an otoendoscope so as to identify an occurrence of otitis media with effusion (OME) (see FIG. 3).

The fraction of *Melissa officinalis* leaf extract according to Example 1 was suspended in 0.5% carboxymethyl cellulose (CMC) and orally administered, while a control group was dosed with 0.5% CMC only.

Right after blocking the eustachian tube (ET), 0.5% CMC (control group, n=11) and the fraction of *Melissa officinalis* leaf extract according to Example 1 (experimental group, n=11) were administered to SD white rats at a dose of 100 mg/kg/day.

The therapeutic effect, histopathological findings and a thickness of middle ear mucosa on otitis media with effusion were evaluated.

The therapeutic effect on otitis media with effusion was defined as Grade II (middle ear cavity fully filled with effusion, indicated as "++"), Grade I (middle ear cavity partially filled with effusion, indicated as "+") and Grade 0 (no effusion, indicated as "O"). The therapeutic effect on otitis media with effusion was identified three times in total. A first identification was made on the third day after blocking the eustachian tube, a second identification was made on the fifth day after blocking the eustachian tube, and a third identification was made on the seventh day after blocking the eustachian tube by using an otoendoscope.

Histopathological findings were obtained by removing the middle ear cavity on the seventh day after blocking the eustachian tube, and observing the extracted middle ear tissue.

A thickness of middle ear mucosa was observed that a bulla was removed on the seventh day after blocking the eustachian tube, and fixed in 10% formalin, and subjected to decalcification and dehydration by using EDTA, and fixed in paraffin, and then subjected to hematoxylin and eosin (HE) stain and masson-trichrome stain. The thickness of subepithelial layer was measured using Image J software by observing 5 places around the most thickened mucosa of the middle ear promontory.

(2) Therapeutic Effect on Otitis Media with Effusion
The therapeutic effect on otitis media with effusion was determined in the control group (0.5% CMC) and the experimental group (the fraction of *Melissa officinalis* leaf extract according to Example 1).

Specifically, referring to Table 3, otitis media with effusion was occurred as Grade II (++) in the control group and the experimental group from a third day after blocking the eustachian tube (first identification).

In the experimental group (the fraction of *Melissa officinalis* leaf extract according to Example 1), a loss of middle ear effusion (MEE) started to be ameliorated from Grade II (++) to Grade I (+) from a fifth day after blocking the eustachian tube (see FIG. 4), and was ameliorated to Grade 0 (90.9%) within seven days in ten out of eleven SD white rats in total (see FIG. 5).

In the control group (0.5% CMC), however, only two out of eleven SD white rats in total were improved to Grade 0 (18.1%), and seven out of eleven rats maintained otitis media with effusion without improvement (63.6%).

TABLE 3

| Otoendoscopy | | Control group | Experimental group | Remark |
|---|---|---|---|---|
| $1^{st}$ identification (on 3rd day after blocking the eustachian tube) | grade 0 | 0 | 0 | |
| | grade I | 0 | 0 | |
| | grade II | 11 | 11 | |
| | Total | 11 | 11 | |
| $2^{nd}$ identification (on 5th day after blocking the eustachian tube) | grade 0 | 0 | 5 | |
| | grade I | 3 | 5 | |
| | grade II | 8 | 0 | |
| | Acute otitis media | 0 | 1 | Excluding data |
| | Total | 11 | 10 | |
| $3^{rd}$ identification (7th day after blocking the eustachian tube) | grade 0 | 2 | 10 | |
| | grade I | 4 | 0 | |
| | grade II | 3 | 0 | |
| | Acute otitis media | 2 | 0 | Excluding data |
| | Total | 9 | 10 | |

(3) Histopathological Findings
Histopathological findings showed that effusion was present in a middle ear cavity with inflammatory cells in the control group (0.5% CMC), while effusion was reabsorbed and thus not observed in the experimental group (the fraction of *Melissa officinalis* leaf extract according to Example 1).

Specifically, the histopathological findings on the middle ear cavity removed on a seventh day after blocking the eustachian tube showed that effusion was not absorbed, but present in the middle ear cavity in the control group (0.5% CMC), while effusion was absorbed in the experimental group (the fraction of *Melissa officinalis* leaf extract according to Example 1) (see FIG. 6).

(4) Evaluation of Thickness of Middle Ear Mucosa
In the experimental group (the fraction of *Melissa officinalis* leaf extract according to Example 1), the thickness of middle ear mucosa was remarkably thinner than that of the control group (0.5% CMC) (see FIG. 7, p<0.05).

Specifically, inflammatory cells were present inside the middle ear cavity of the control group (0.5% CMC), while inflammatory cells were not seen in the experimental group (the fraction of *Melissa officinalis* leaf extract according to Example 1), and the middle ear mucosa became significantly thinner in the experimental group compared to the control group.

5) Evaluation of Inflammatory Factors
IL-23 genes up-regulated by LPS were significantly decreased in the experimental group (the fraction of *Melissa officinalis* leaf extract according to Example 1) (see FIG. 8), and TNF-α genes up-regulated by LPS were significantly decreased in the experimental group (the fraction of *Melissa officinalis* leaf extract according to Example 1) (see FIG. 9).

The invention claimed is:

1. A method for preventing or treating otitis media with effusion, the method comprising:
   administering to a subject in need thereof a therapeutically effective amount of a pharmaceutical composition comprising a fraction of *Melissa officinalis* leaf extract.

2. The method according to claim 1, wherein the fraction of the extract is obtained by extracting *Melissa officinalis* leaves with 50 to 100% alcohol, concentrating, fractionating with ethyl acetate, and drying.

3. The method according to claim 1, wherein the fraction of *Melissa officinalis* leaf extract is an ethyl acetate fraction of ethanol extract of *Melissa officinalis* leaves.

* * * * *